(12) United States Patent
Preuß

(10) Patent No.: US 11,517,192 B2
(45) Date of Patent: Dec. 6, 2022

(54) STERILE ENDOSCOPE SHEATH

(71) Applicant: avateramedical GmbH, Jena (DE)

(72) Inventor: Peter Preuß, Jena (DE)

(73) Assignee: Avateramedical GmbH

( * ) Notice: Subject to any disclaimer, the term of this patent is extended or adjusted under 35 U.S.C. 154(b) by 451 days.

(21) Appl. No.: 16/395,496

(22) Filed: Apr. 26, 2019

(65) Prior Publication Data

US 2019/0328220 A1    Oct. 31, 2019

(30) Foreign Application Priority Data

Apr. 26, 2018 (DE) .......................... 102018110095.7

(51) Int. Cl.
*A61B 1/12* (2006.01)
*A61B 1/00* (2006.01)
*G02B 5/20* (2006.01)

(52) U.S. Cl.
CPC .......... *A61B 1/128* (2013.01); *A61B 1/00055* (2013.01); *A61B 1/00142* (2013.01); *A61B 1/00165* (2013.01); *G02B 5/208* (2013.01)

(58) Field of Classification Search
CPC ... A61B 1/00142; A61B 1/0676; A61B 1/128; A61B 1/00055; A61B 1/00165; A61B 1/00135; A61B 1/00096; A61B 1/00144; A61B 1/00057; A61B 1/07; A61B 1/00097; G02B 5/208
USPC ........................................................ 600/114
See application file for complete search history.

(56) References Cited

U.S. PATENT DOCUMENTS

| 2005/0283048 | A1 | 12/2005 | Gill | |
|---|---|---|---|---|
| 2013/0218147 | A1 | 8/2013 | Brown | |
| 2014/0200406 | A1* | 7/2014 | Bennett | A61B 1/127 600/109 |
| 2015/0018613 | A1 | 1/2015 | Hollenbeck | |
| 2017/0143214 | A1* | 5/2017 | Garibotto | A61B 5/4233 |
| 2017/0188802 | A1* | 7/2017 | Lawrence | A61B 1/00016 |

FOREIGN PATENT DOCUMENTS

| DE | 2129094 | | 12/1971 | |
|---|---|---|---|---|
| DE | 2932116 | A1 | 2/1981 | |
| DE | 102010022429 | A1 | 12/2011 | |
| DE | 102010053814 | A1 | 6/2012 | |
| DE | 102016007669 | A1 * | 12/2017 | A61B 1/00096 |
| DE | 102016007669 | A1 | 12/2017 | |
| EP | 820250 | | 1/1998 | |
| EP | 0904725 | A1 | 3/1999 | |

(Continued)

OTHER PUBLICATIONS

"Albert Schlisser, Mid-infrared frequency combs, Jul. 2012, Nature Photonics, vol. 6, p. 1" (Year: 2012).*

(Continued)

*Primary Examiner* — Michael J Carey
*Assistant Examiner* — Christen A. Sharpless
(74) *Attorney, Agent, or Firm* — McGarry Bair PC

(57) ABSTRACT

An arrangement for sterile handling of a non-sterile endoscope in a sterile environment. The arrangement includes a sterile endoscope sheath, and the non-sterile endoscope. The sterile endoscope sheath has an optical element arranged at a distal end of the sterile endoscope sheath. The non-sterile endoscope has an endoscope shaft with an optical element arranged at a distal end of the endoscope shaft.

9 Claims, 7 Drawing Sheets

(56) References Cited

FOREIGN PATENT DOCUMENTS

WO   20150187626 A1   10/2015
WO   WO-2015187626 A1 * 12/2015 ........... A61B 5/0086

OTHER PUBLICATIONS

Office Action and search report from corresponding European application No. 19169707.7, dated Aug. 21, 2019.
German Patent Office, Office Action re Corresponding Application No. 102018110095.7, dated Feb. 27, 2019, 14 pages, Munchen.

* cited by examiner

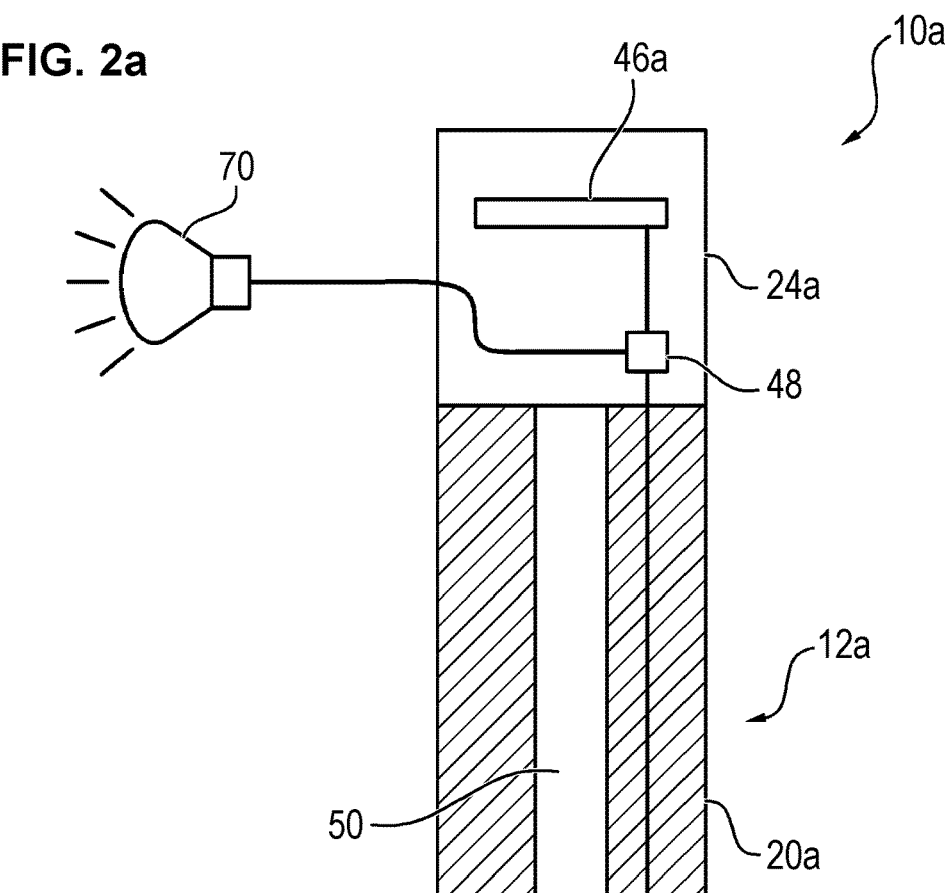
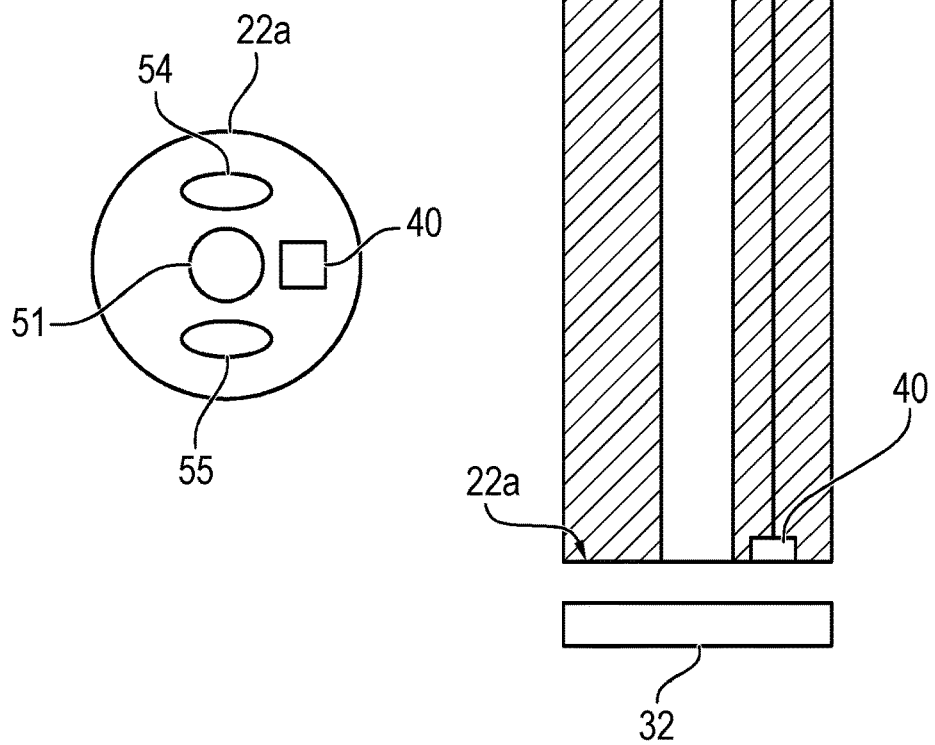

STERILE ENDOSCOPE SHEATH

CROSS REFERENCE TO RELATED APPLICATION

This application claims the benefit of German Application DE 10 2018 110 095.7, filed on Apr. 26, 2018, which is incorporated herein in its entirety.

BACKGROUND

The invention relates to a sterile endoscope sheath for a non-sterile endoscope. The endoscope sheath comprises an optical element arranged at a distal end of the endoscope sheath, i.e. an end facing the patient. Further, the invention relates to an arrangement for the sterile handling of a non-sterile endoscope in a sterile environment.

Known arrangements for the sterile handling of a non-sterile endoscope in a sterile environment, such as an operating room, comprise a non-sterile endoscope and a sterile endoscope sheath having an optical element arranged at a distal end. The endoscope sheath is typically a sterile disposable article or an endoscope sheath which can again be sterilized, i.e. reprocessed. Such an endoscope sheath is, for example, known from document DE 10 2010 022 429 A1. The endoscope sheath has two sheath parts which are mechanically connectable to each other in a releasable and fluid-tight manner. Further, document DE 10 2010 053 814 A1 discloses an endoscope for medical purposes, which can be inserted into a sterilized housing.

From document EP 0 904 725 A1, an endoscope having a replaceable shaft is known, which is formed as a sterile disposable article. The disadvantages of this endoscope are the comparably high costs incurred by the replacement of the shaft with every use.

The optical element of known endoscope sheaths is transparent to visible light. Therefore, an illumination of the situs, i.e. the opened operating field, takes place by illumination light that is emitted from a distal end of an endoscope arranged in an endoscope sheath. A contamination of the optical element, by residues for example, however results in that the optical element becomes opaque to the illumination light at least in parts and absorbs a part of the illumination light. The absorbed illumination light is converted into heat and causes a strong heating of the optical element, by which considerable damage to organs may occur. The disadvantage of endoscope sheaths known up to now is that this heating cannot be detected.

From document US 2014/0200406 A1, an endoscope is known, in which the fogging of a distally arranged optical element is prevented by means of infrared light. The optical element is configured such that it absorbs the infrared light. The optical element is heated by the absorption, as a result whereof fogging is prevented and/or already present condensation water is evaporated.

From document DE 21 29 094 A1, an alarm system for monitoring the temperature of uranium fuel rods in a storage is known. The alarm system has an optical system for capturing electromagnetic radiation in the infrared range originating from the storage and an infrared detector with an upstream filter that is transparent to an infrared wavelength range.

Further, from document EP 0 820 250 B1, a system for the endoscopic diagnosis is known, which uses both visible and infrared light for imaging.

SUMMARY OF THE INVENTION

Starting from the known prior art, it is the object of the invention to specify an endoscope sheath in which the temperature of an optical element arranged at a distal end of the endoscope sheath can reliably be determined. In addition, an arrangement for the sterile handling of a non-sterile endoscope in a sterile environment is to be specified.

This object is solved by an endoscope sheath having the features of claim 1 and by an arrangement having the features of claim 4. Advantageous developments are specified in the dependent claims.

The inventive sterile endoscope sheath for a non-sterile endoscope has an optical element arranged at a distal end of the endoscope sheath. The optical element absorbs electromagnetic radiation in an absorption wavelength range lying in the mid-infrared wavelength range.

In this document, mid-infrared wavelength range means a wavelength range between 3 µm and 50 µm. This wavelength range corresponds to the wavelength range of heat radiation at temperatures prevailing on the earth. In this document, distal refers to a direction facing the patient and proximal refers to a direction facing away from the patient. When referring to an element, an object or an arrangement, distal and proximal are used in relation to the intended position of the element, the object and the arrangement, respectively.

Since the optical element absorbs the electromagnetic radiation in the absorption wavelength range, the optical element has a very low degree of reflection and a very high degree of emission in the absorption wavelength range. The optical element is so to speak a closed cavity or a black-body radiator for electromagnetic radiation in the absorption wavelength range. Thus, the electromagnetic radiation in the absorption wavelength range originating from the optical element corresponds substantially to the heat radiation originating from the optical element, which heat radiation is only dependent on the temperature of the optical element. The optical element is further opaque to the electromagnetic radiation in the absorption wavelength range. Sources of electromagnetic radiation in the absorption wavelength range, such as organs or other surgical instruments in the situs of a patient, are covered by the optical element. Thus, it is possible to exclusively detect the heat radiation emitted by the optical element itself with the aid of a sensor. Since from the spectrum of this radiation the temperature of the optical element can be determined, it is possible in the case of the inventive endoscope sheath to determine the temperature of the optical element in a reliable manner.

It is advantageous when the optical element is transparent in at least one optical wavelength range outside the absorption wavelength range. Preferably, the at least one optical wavelength range lies in the range of the visible light, i.e. in a range from 380 nm to 780 nm. This makes it possible to use the optical element, for example in connection with an endoscope for the imaging in the optical field, without this causing interferences in the imaging.

Further, it is advantageous when the absorption wavelength range is a wavelength range from 9 µm to 10 µm, preferably from 8 µm to 12 µm, particularly preferred from 8 µm to 14 µm. In the wavelength range from 9 µm to 10 µm the maxima of heat radiation spectra of black bodies with the temperatures from 17° C. to 48° C. lie. By a measurement of the electromagnetic radiation in this wavelength range originating from the optical element it is possible to determine when the optical element heats up to a temperature above the body temperature of about 37° C. In the preferred wavelength range from 8 µm to 12 µm the maxima of heat radiation spectra of black bodies with the temperatures from −31° C. to 89° C. lie. Thus, it is possible to determine when the optical element heats up to a temperature above the coagulation temperature of tissue, i.e. the temperature at which proteins coagulate, of about 60° C. When the endoscope heats up to a temperature above the coagulation temperature, necrosis may occur on tissue in particular of organs with which the optical element comes into contact. The particularly preferred wavelength range from 8 μm to 14 μm comprises the maxima of heat radiation spectra of black bodies with the temperatures from −60° C. to 89° C. The measurement of a broad spectrum allows an even more reliable determination of the temperature of the optical element.

The invention further relates to an arrangement for the sterile handling of a non-sterile endoscope in a sterile environment. The inventive arrangement comprises an inventive sterile endoscope sheath according to claim 1 or according to an advantageous development and a non-sterile endoscope. The endoscope comprises an endoscope shaft and an optical element arranged at a distal end of the endoscope shaft. The optical element of the endoscope is transparent to electromagnetic radiation in the absorption wavelength range. The endoscope is accommodated in the endoscope sheath which shields the endoscope against the environment in a sterile manner.

The use of the non-sterile endoscope in connection with the sterile endoscope sheath is a cost-efficient alternative to the re-sterilization of endoscopes that can be used multiple times or to the use of disposable endoscopes. Further, the inventive endoscope sheath makes it possible to determine the temperature of the optical element in a reliable manner.

It is advantageous when the endoscope has a first sensor element which detects an electromagnetic radiation in the absorption wavelength range originating from the optical element of the endoscope sheath. Preferably, the sensor element is configured to detect the electromagnetic radiation in the absorption wavelength range originating from the optical element in a spectrally resolved manner. From the electromagnetic radiation detected by the first sensor element, the temperature of the optical element can be determined.

Preferably, the arrangement has a control unit which determines a temperature of the optical element of the endoscope sheath on the basis of the electromagnetic radiation detected by the first sensor element. The temperature determined by the control unit can, for example, be output by an output unit. As a result thereof, the temperature can automatically be monitored and the endoscope can be removed from the body of the patient or the illumination can be turned off before the temperature of the optical element reaches a value at which the patient may be at risk.

It is advantageous when the arrangement has an output unit which outputs an acoustic and/or optical warning signal when the determined temperature of the optical element of the endoscope sheath reaches and/or exceeds a preset value. As a result, a surgeon need not monitor the temperature of the optical element himself/herself and may concentrate on carrying out the medical intervention on the patient. Preferably, the preset value is below a temperature at which a coagulation or necrosis of tissue occurs. Thus, the endoscope may be removed from the body of the patient in due course or the illumination light may be turned off before the patient is at risk.

Further, it is advantageous when the endoscope shaft includes a first optical fiber which is optically connected to the first sensor element and which guides electromagnetic radiation in the absorption wavelength range entering the distal end of the endoscope shaft to the first sensor element. By way of the optical fiber it is possible to arrange the first sensor element in a proximal part of the endoscope, for example a handpiece. As a result, a compact structure of the endoscope is made possible.

Alternatively, the endoscope has a beam splitter which couples the electromagnetic radiation in the absorption wavelength range out of an observation optical system of the endoscope and directs it onto the first sensor element. The electromagnetic radiation in the absorption wavelength range entering the distal end of the endoscope shaft is guided to the proximal end of the endoscope by the observation optical system instead of the first optical fiber. By the use of the observation optical system the necessity to provide an own optical channel for the electromagnetic radiation in the absorption wavelength range can be dispensed with. As a result thereof, the structure of the endoscope becomes more compact and the endoscope can be produced more cost-efficiently.

Further, it is advantageous when the endoscope has a second sensor element detecting electromagnetic radiation in the absorption wavelength range and the endoscope shaft includes a second optical fiber which is optically connected to the second sensor element and which guides electromagnetic radiation in the absorption wavelength range from the distal end of the endoscope shaft to the second sensor element. Preferably, the second optical fiber is optically closed at a distal end. The only radiation guided by the optical fiber is the heat radiation originating from the closure of the second optical fiber. As a result, a reference channel is formed with which the temperature of the endoscope, in particular of the distal end of the endoscope, can be determined. A heating of the optical element of the endoscope sheath causes, by way of heat conduction, a heating of the distal end of the endoscope. Since the heat conduction process requires time, it can be distinguished by way of the reference channel whether a determined heating of the optical element only takes place for a short period of time, for example by a contact of the optical element with a laser scalpel, or for a long period of time, for example by a contamination of the optical element and an absorption of illumination light caused thereby.

It is advantageous when the control unit determines a temperature of the optical element of the endoscope sheath on the basis of the electromagnetic radiation detected by the first sensor element and determines a temperature of the optical element of the endoscope on the basis of the electromagnetic radiation detected by the second sensor element. Preferably, an output unit outputs an acoustic and/or optical warning signal when the determined temperature of the optical element of the endoscope sheath and the determined temperature of the optical element of the endoscope reach and/or exceed a respective preset value. As a result, it is prevented that error warnings occur when the optical element only heats up for a short period of time, for example by the contact with another surgical instrument. The determination of a temperature of the optical element that is critical for a patient is thus even more reliable.

Alternatively, the control unit determines a difference between the determined temperature of the optical element of the endoscope sheath and the determined temperature of the optical element of the endoscope. Preferably, the output unit outputs an acoustic or optical warning signal when the determined temperature of the optical element of the endoscope sheath reaches and/or exceeds a preset value and when the determined difference between the determined temperature of the optical element of the endoscope sheath and the determined temperature of the optical element of the endoscope reaches and/or falls below a preset value.

Further, it is advantageous when the optical element of the endoscope sheath has at least an area which is transparent to electromagnetic radiation in the absorption wavelength range. Preferably, the endoscope has a third sensor element. The endoscope shaft preferably includes a third optical fiber which is optically coupled to the third sensor element. A distal end of the third optical fiber is arranged opposite to the at least one area. The third optical fiber guides electromagnetic radiation in the absorption wavelength range entering the distal end of the third optical fiber to the third sensor element. Electromagnetic radiation in the absorption wavelength range which is, for example, emitted by sources in the situs can freely pass the optical element in the at least one area and is guided through the third optical fiber to the third sensor element and detected thereby. Since from the spectrum of this radiation the temperature of the source in the situs can be determined, it is possible to perform a temperature measurement in the situs, for example for diagnostic purposes. The third sensor element may be an image sensor. As a result, the electromagnetic radiation in the absorption wavelength range detected by the third sensor element can be used for imaging.

When providing different optical elements in different endoscope sheaths, the imaging of the light detected with the aid of the endoscope can be varied by selecting the endoscope sheath so that the optical image capturing properties of the endoscope may be varied by selecting the sheath.

The endoscope may be a mono-endoscope, i.e. an endoscope with only one optical channel, or a stereoscopic endoscope.

Further features and advantages of the invention result from the following description which explains the invention in more detail on the basis of embodiments in connection with the enclosed Figures.

DRAWINGS

FIG. 2a shows a schematic sectional view of an arrangement with a mono-endoscope according to a second embodiment;

FIG. 2b shows a schematic illustration of the mono-endoscope according to FIG. 2a, as viewed from a distal side;

DESCRIPTION

Figure 1:
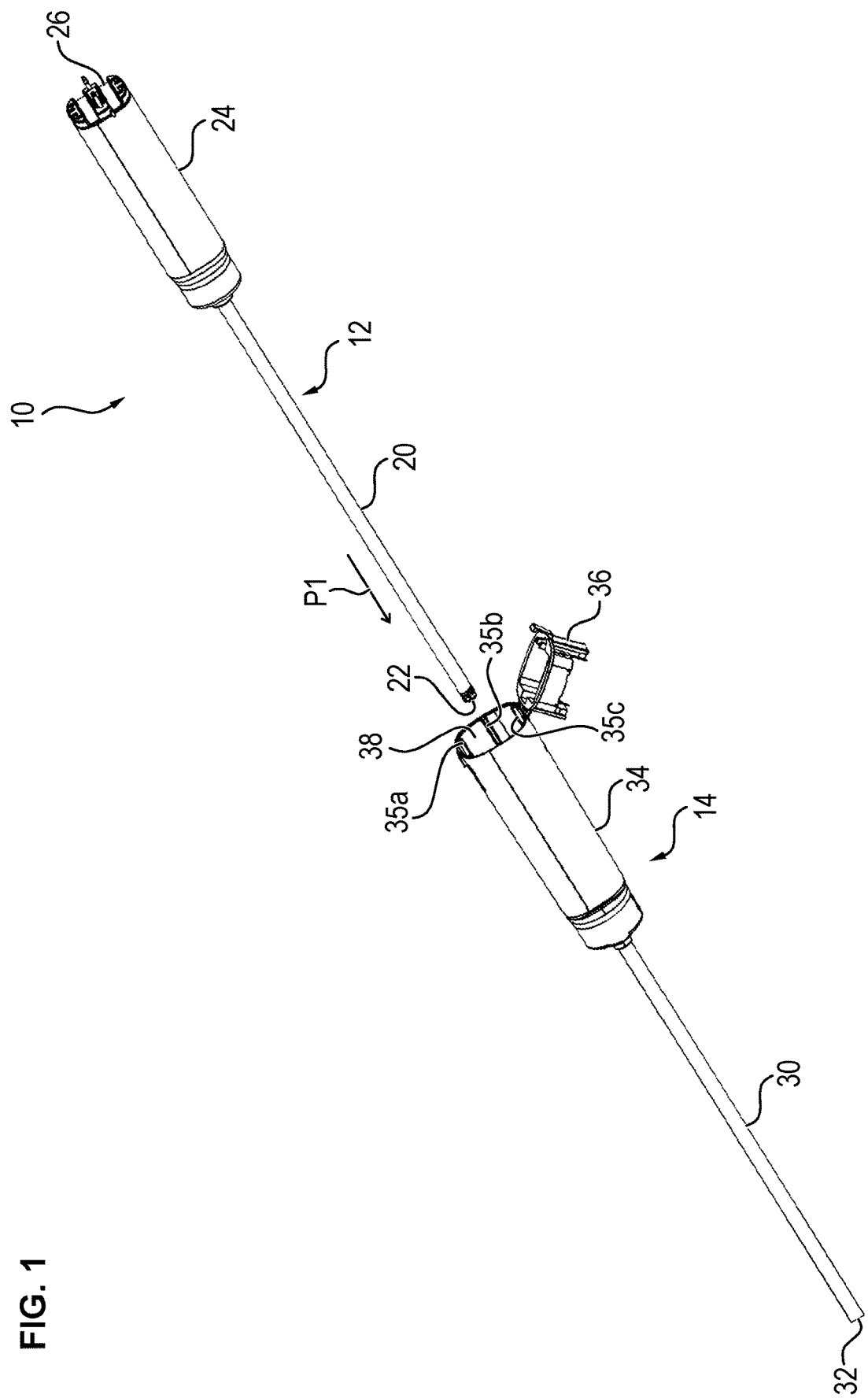
FIG. 1 shows an arrangement for the sterile handling of a non-sterile endoscope in a sterile environment with a sterile endoscope sheath according to a first embodiment.

FIG. 1 shows a perspective illustration of an arrangement 10 for the sterile handling of a non-sterile endoscope 12 in a sterile environment according to a first embodiment. In addition to the endoscope 12, the arrangement 10 comprises a sterile endoscope sheath 14.

The endoscope 12 has an endoscope body 24 arranged at a proximal end of an endoscope shaft 20. The endoscope 12, in particular the inner structure of the endoscope 12, is described in the following in more detail with reference to FIGS. 2a, 2b, 3a, 3b, 4a, 4b, 5a, 5b, 6a, 6b, 7a and 7b.

The endoscope sheath 14 comprises a front part 30 for receiving the endoscope shaft 20 at least partially insertable into a body of a patient. The front part 30 of the endoscope sheath 14 is closed at a distal end with the aid of an optical element 32 that absorbs electromagnetic radiation in an absorption wavelength range from 8 μm to 14 μm and is transparent in an optical wavelength range from 380 nm to 780 nm. Since the optical element 32 absorbs the electromagnetic radiation in the absorption wavelength range, it has a very low degree of reflection and a very high degree of emission in the absorption wavelength range. Thus, the electromagnetic radiation in the absorption wavelength range originating from the optical element 32 substantially corresponds to the heat radiation originating from the optical element 32, which heat radiation is only dependent on the temperature of the optical element 32. From the spectrum of this radiation, the temperature of the optical element 32 can be determined.

The endoscope sheath 14 further comprises a middle part 34 for receiving the endoscope body 24 and a closing element 28 with a sterile lock connected to the middle part 34. By the closing element 36 a feeding and removal opening 38 of the endoscope sheath 14 for inserting and removing the endoscope 12 into and from the endoscope sheath 14, respectively, is formed. With the aid of the sterile lock, a contact area 26 of the endoscope 12 with electric contact and optical connecting elements is shielded in a sterile manner.

For receiving the endoscope 12 in the endoscope sheath 14, the endoscope 12 is inserted in the direction of the arrow P1 through the open feeding and removal opening 38 into the endoscope sheath 14. For this, the endoscope shaft 20 is first inserted into the feeding and removal opening 38 and subsequently pushed up into the front part 30 of the endoscope sheath 14 so that a tip 22 of the endoscope shaft 20 is arranged opposite to the optical element 32 of the endoscope sheath 14 arranged at the distal end of the front part 30. When inserting an endoscope body 24 through the feeding and removal opening 38 into the middle part 34 of the endoscope sheath 14, the endoscope body 24 is guided by guiding webs 35a to 35c present on the inside in the middle part 34 of the endoscope sheath 14 and held in a predefined position in the middle part 34 of the endoscope sheath 14.

FIG. 2a shows a schematic sectional view of an arrangement 10a according to a second embodiment. Same elements or elements having the same function are identified with the same reference signs. The arrangement 10a comprises a mono-endoscope 12a having a first sensor element 40, an endoscope sheath 14 according to FIG. 1, of which in FIG. 2a only the optical element 32 is shown, and an output unit 70. The non-sterile mono-endoscope 12a is received by the sterile endoscope sheath 14 and thus shielded in a sterile manner against the environment.

The mono-endoscope 12a has an endoscope shaft 20a projecting in distal direction from an endoscope body 24a, at the distal tip 22a of which shaft the first sensor element 40 is arranged. The endoscope shaft 20a further comprises a first observation optical system 50. The endoscope body 24a connects to the endoscope shaft 20a at the proximal end thereof. In the endoscope body 24a, in particular a control unit 48 and an image sensor 46a are arranged.

The electromagnetic radiation in the absorption wavelength range originating from the optical element 32 is substantially the heat radiation of the optical element 32, which heat radiation is only dependent on its temperature. This radiation is detected by the first sensor element 40 arranged at the distal tip 22a of the endoscope shaft 20a. From the spectrum of the detected radiation, the control unit 48 determines the temperature of the optical element 32. When the temperature of the optical element 32 determined by the control unit 48 exceeds a preset limit value, the control unit 48 controls the output unit 70 such that it outputs an optical and/or acoustic warning signal.

The first observation optical system 50 forms an optical channel which guides observation light in an optical wavelength range entering the tip 22a of the endoscope shaft 20a from the distal end of the endoscope shaft 20a to the proximal end of the endoscope shaft 20a. After passage through the first observation optical system 50, the observation light is incident on the image sensor 16a and is converted by it into a signal or data. The signal or the data is further processed by the control unit 48 for image display. As a result thereof, an observation of an area distal to the tip 22a is possible. Alternatively, the signal or the data may also be further processed by another control unit outside the endoscope 12a for image display.

FIG. 2b shows a schematic illustration of the mono-endoscope 12a according to FIG. 2a, as viewed from the distal side, i.e. the tip 22a of the mono-endoscope 12a. The distal end 51 of the first observation optical system 50 is arranged in the center of the tip 22a. In the illustration of FIG. 2b, one distal end 54, 55 of an illumination optical system for illuminating the area distal to the tip 22a each is arranged above and below the distal end 51 of the first illumination optical system 50. In the illustration of FIG. 2b, the first sensor element 40 is arranged to the right of the distal end 51 of the observation optical system 50.

Figure 3A:
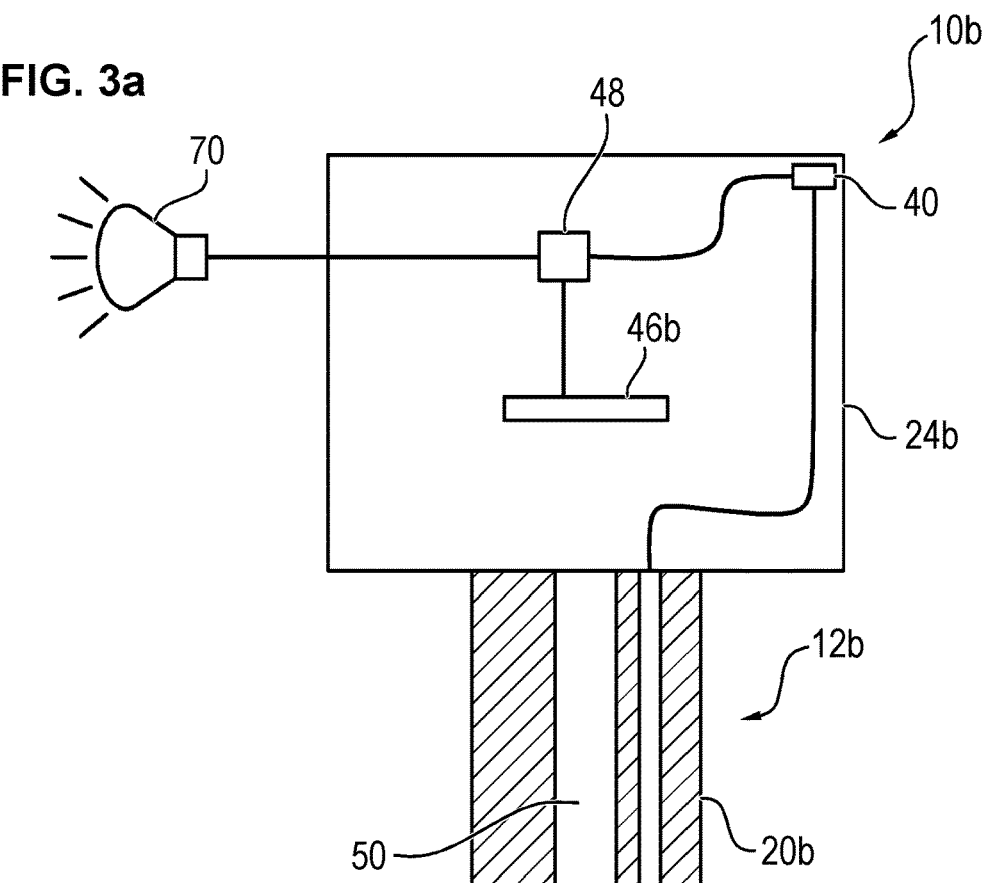
FIG. 3a shows a sectional view of an arrangement with a mono-endoscope according to a third embodiment.

FIG. 3a shows a schematic sectional view of an arrangement 10b according to a third embodiment. The arrangement 10b comprises a mono-endoscope 12b having the first sensor element 40. The arrangement 10b further comprises a first optical fiber 56 which is optically connected to the first senor element 40. Further, the arrangement 10b comprises the endoscope sheath 14 according to FIG. 1, of which in FIG. 2a only the optical element 32 is shown, and the output unit 70. The non-sterile mono-endoscope 12b is received in the sterile endoscope sheath 14 and is shielded by it against the environment in a sterile manner. The arrangement 10b according to the third embodiment according to FIG. 3a differs from the arrangement 10a according to the second embodiment of FIG. 2a substantially by a first optical fiber 56.

The endoscope shaft 20b of the mono-endoscope 12b comprises the first observation optical system 50 and the first optical fiber 56. The mono-endoscope 12b further has an endoscope body 24b arranged at the proximal end of the endoscope shaft 20b, in which endoscope body 24b in particular the first sensor element 40, the control unit 48 and the image sensor 46b are arranged.

The electromagnetic radiation in the absorption wavelength range originating from the optical element 32 enters the distal end 57 of the first optical fiber 56 arranged at the distal tip 22b of the endoscope shaft 20a. The first optical fiber 56 guides the electromagnetic radiation in the absorption wavelength range from its distal end 57 to the first sensor element 40 that detects this radiation. From the spectrum of the detected radiation, the control unit 48 determines the temperature of the optical element 32. When the temperature of the optical element 32 determined by the control unit 48 exceeds a preset limit value, the control unit 48 controls the output unit 70 such that it outputs an optical and/or acoustic warning signal.

Figure 3B:
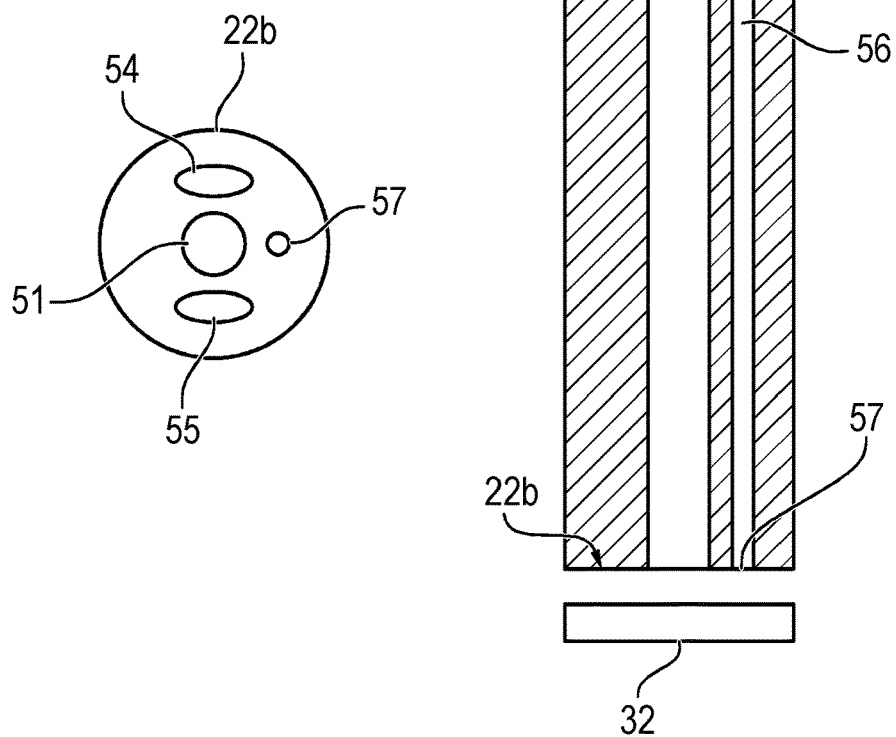
FIG. 3b shows a schematic illustration of a mono-endoscope according to FIG. 3a, as viewed from a distal side.

FIG. 3b shows a schematic illustration of the mono-endoscope 12b according to FIG. 3a, as viewed from a distal side. FIG. 3a in particular shows the tip 22b of the mono-endoscope 12b. In the illustration of FIG. 3b, the distal end 57 of the first optical fiber 56 is arranged to the right of the distal end 51 of the observation optical system 50.

Figure 4A:
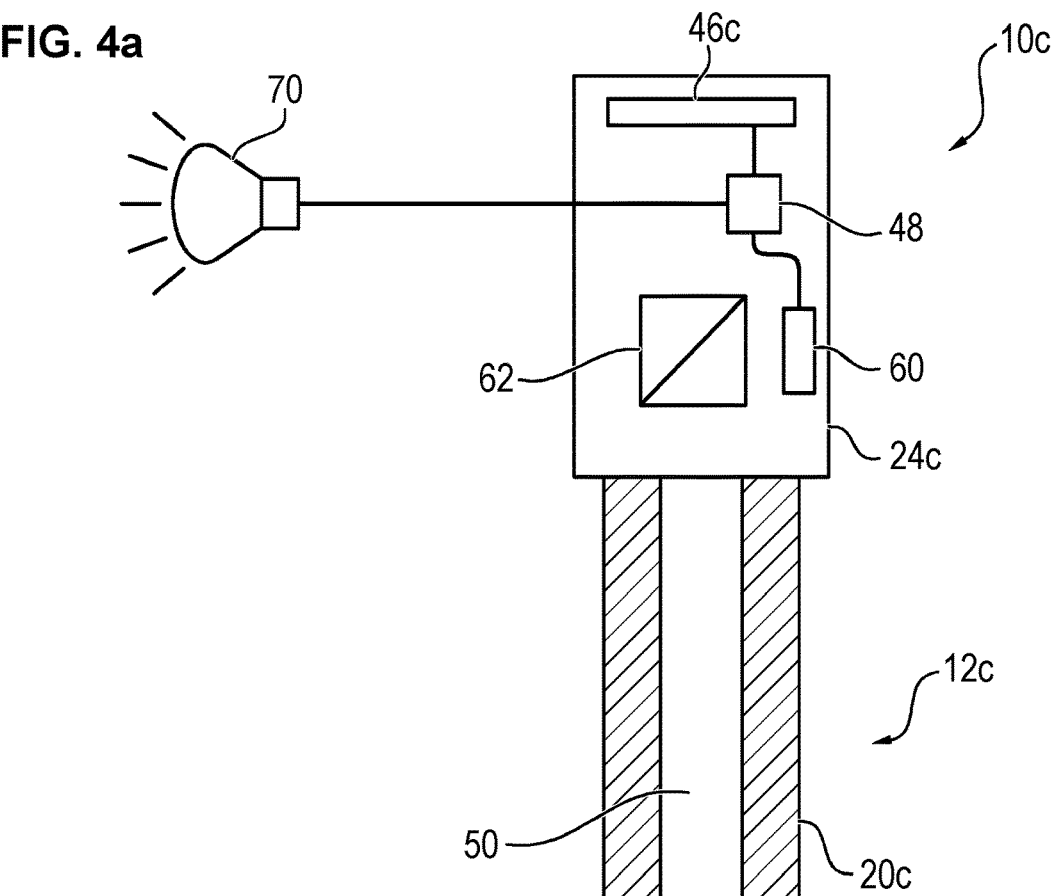
FIG. 4a shows a schematic sectional view of an arrangement with a mono-endoscope according to a fourth embodiment.

FIG. 4a shows a schematic sectional view of an arrangement 10c according to a fourth embodiment. The arrangement comprises a mono-endoscope 12c having the first sensor element 40 and a beam splitter 62, an endoscope sheath 14 according to FIG. 1, of which in FIG. 3a only the optical element 32 is shown, as well as the output unit 70. The non-sterile mono-endoscope 12c is received by the sterile endoscope sheath 14 and shielded by it against the environment. The arrangement 10c according to the fourth embodiment according to FIG. 3a differs from the arrangement 10a according to the second embodiment according to FIG. 2a substantially by the provision of a beam splitter 62.

The endoscope shaft 20c includes the first observation optical system 50. The mono-endoscope 12c further has an endoscope body 24c including an image sensor 46c, the endoscope body 24c being arranged at the proximal end of the endoscope shaft 20c, in which in particular the first sensor element 40, the control unit 48 and the beam splitter 62 are arranged.

The electromagnetic radiation in the absorption wavelength range originating from the optical element 32 enters the distal end 51 of the first observation optical system 50 arranged at a distal tip 22c of the endoscope shaft 20c. The first observation optical system 50 guides the electromagnetic radiation in the absorption wavelength range from its distal end 51 to the beam splitter 62. The beam splitter 62 directs the electromagnetic radiation in the absorption wavelength range to the first sensor element 40 that detects this radiation. From the spectrum of the detected radiation, the control unit 48 determines the temperature of the optical element 32. When the temperature of the optical element 32 determined by the control unit 48 exceeds a preset limit value, the control unit 48 controls the output unit 70 such that it outputs an optical and/or acoustic warning signal.

Figure 4B:
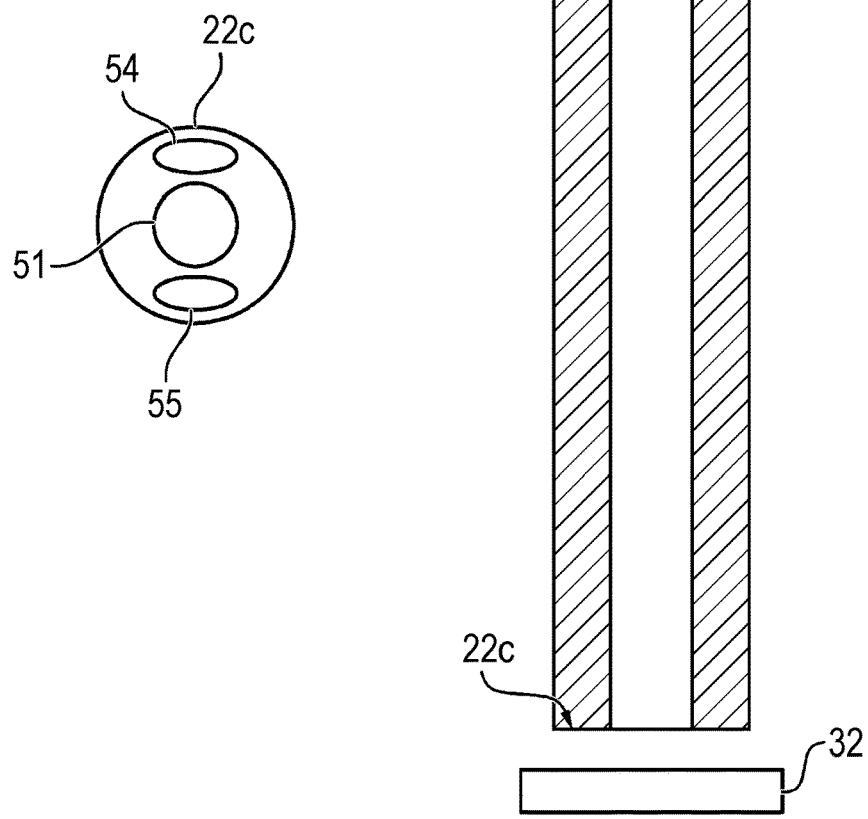
FIG. 4b shows a schematic illustration of the mono-endoscope according to FIG. 4a, as viewed from a distal side.

FIG. 4b shows a schematic illustration of the mono-endoscope 12c according to FIG. 4a, as viewed from the distal side. The distal end 51 of the first observation optical system 50 is arranged centrally. In FIG. 4b, one distal end 54, 55 of an illumination optical system for illuminating the area distal to the tip 22c each is illustrated above and below the distal end 51 of the first observation optical system 50.

Figure 5A:
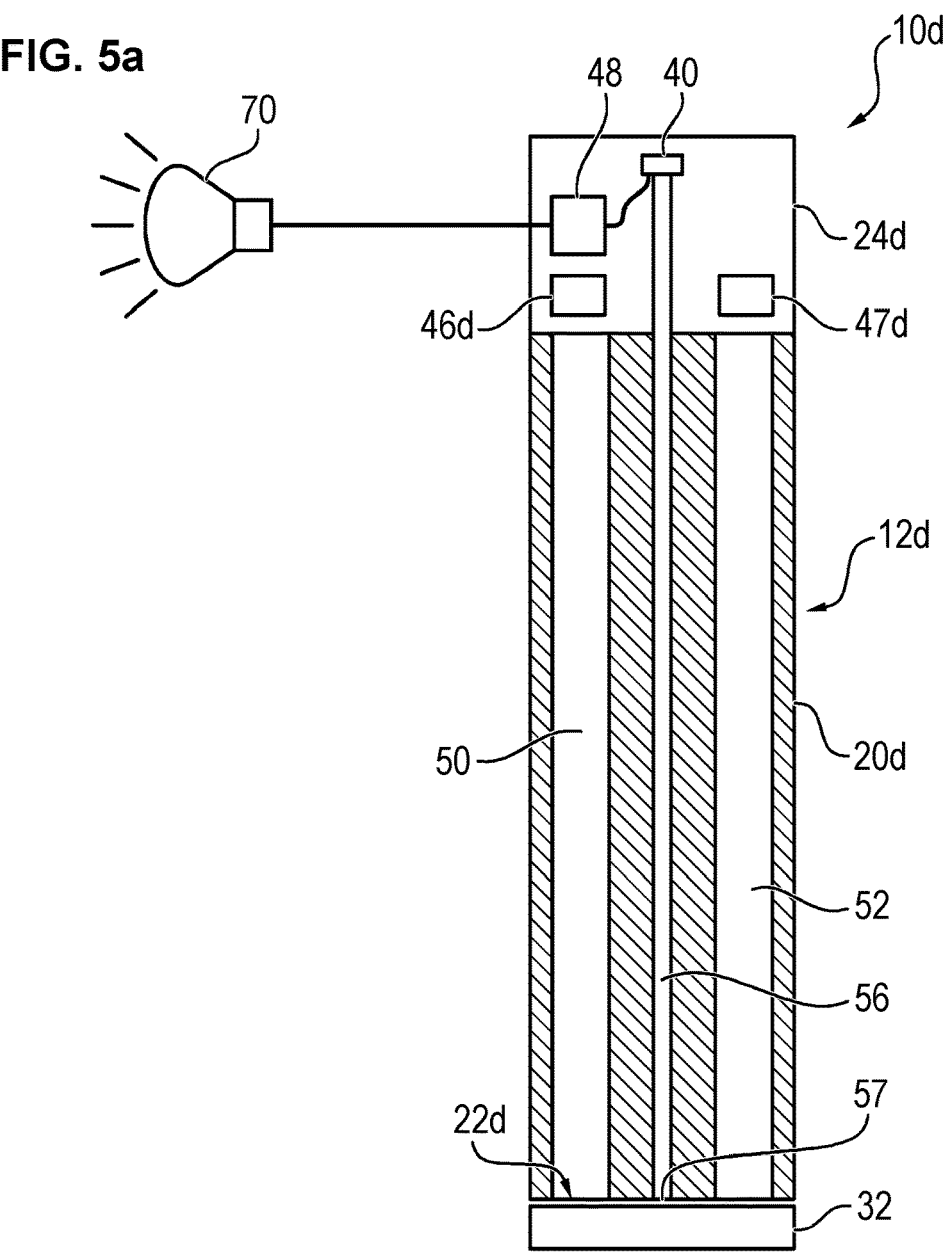
FIG. 5a shows a schematic sectional view of an arrangement with a stereoscopic endoscope according to a fifth embodiment.

FIG. 5a shows a schematic sectional view of an arrangement 10d according to a fifth embodiment. The arrangement 10d comprises a stereoscopic endoscope 12d having the first sensor element 40 and the first optical fiber 56. The arrangement 10d further comprises the endoscope sheath 14 according to FIG. 1, of which in FIG. 5a only the optical element 32 is shown, and the output unit 70. The non-sterile endoscope 12d is received in the sterile endoscope sheath 14 and is shielded by it against the environment.

The endoscope shaft 20d comprises the first observation optical system 50, a second observation optical system 52 and the first optical fiber 56. The endoscope 12d further has an endoscope body 24d including a first image sensor 46d and a second image sensor 47d, the endoscope body 24d arranged at the proximal end of the endoscope shaft 20b, in which endoscope body in particular the first sensor element 40 and the control unit 48 are arranged.

The electromagnetic radiation in the absorption wavelength range originating from the optical element 32 enters the distal end 57 of the first optical fiber 56 arranged at a distal tip 22d of the endoscope shaft 20d. The first optical fiber 56 guides the electromagnetic radiation in the absorption wavelength range from its distal end 57 to the first sensor element 40 that detects this radiation. From the spectrum of the detected radiation, the control unit 48 determines the temperature of the optical element 32. When the temperature of the optical element 32 determined by the control unit 48 exceeds a preset limit value, the control unit 48 controls the output unit 70 such that it outputs an optical and/or acoustic warning signal.

The first observation optical system 50 and the second observation optical system 52 each form an optical channel which guides observation light in an optical wavelength range entering the tip 22d of the endoscope shaft 20d from the distal end of the endoscope shaft 20d to the proximal end of the endoscope shaft 20d. As a result, a stereoscopic observation of an area distal to the tip 22d is possible.

Figure 5B:
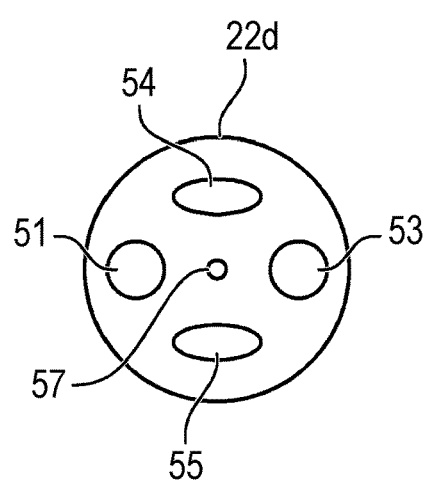
FIG. 5b shows a schematic illustration of the stereoscopic endoscope according to FIG. 5a, as viewed from a distal side.

FIG. 5b shows a schematic sectional view of the stereoscopic endoscope 12d according to FIG. 5a, as viewed from a distal side. The distal end 57 of the first optical fiber 56 is arranged centrally in the tip 22d of the endoscope 12d. In the illustration of FIG. 5b, one distal end 54, 55 of the illumination optical system for illuminating the area distal to the tip 22d each is arranged above and below the distal end 57 of the first optical fiber 56. To the left of the distal end 57 of the first optical fiber 56, a distal end 51 of the first observation optical system 50 is arranged. To the right of the distal end 57 of the first optical fiber 56, a distal end 53 of the second observation optical system 53 is arranged.

Figure 6A:
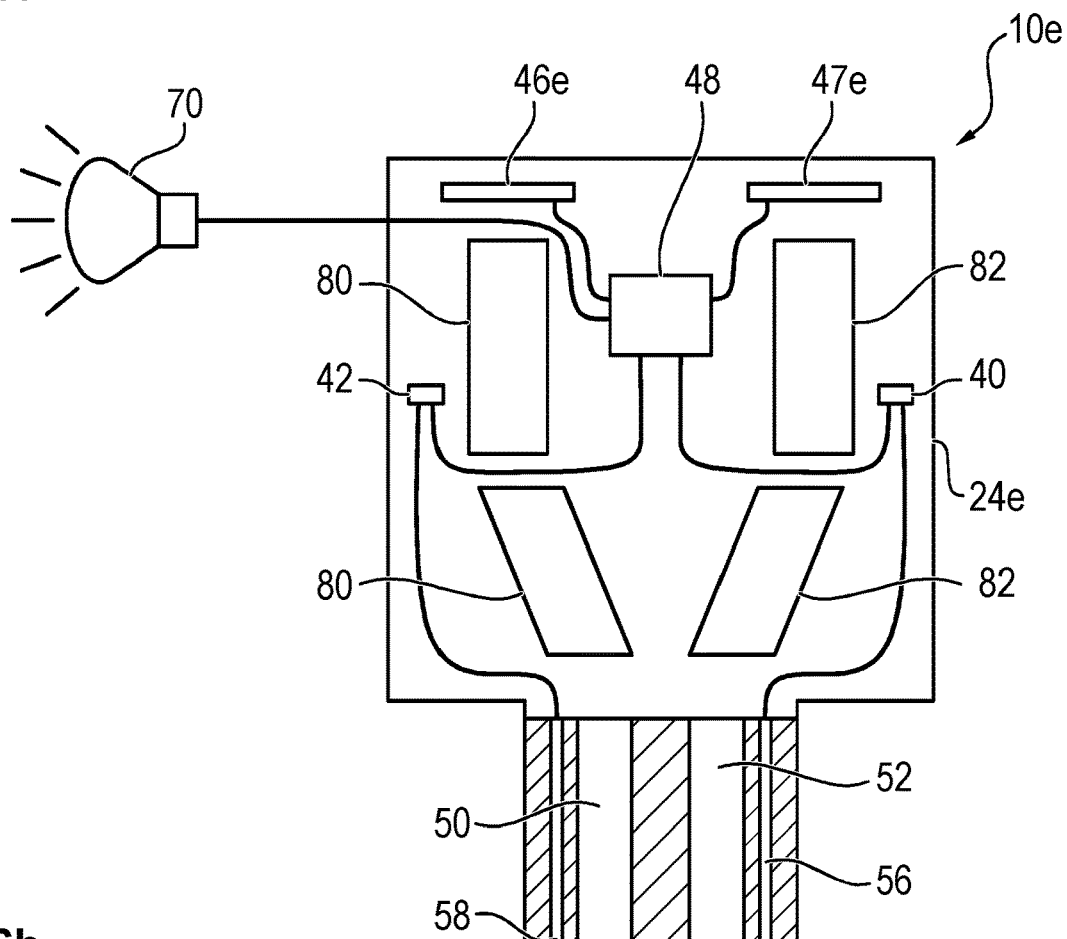
FIG. 6a shows a schematic sectional view of an arrangement with a stereoscopic endoscope according to a sixth embodiment.
Figure 6B:
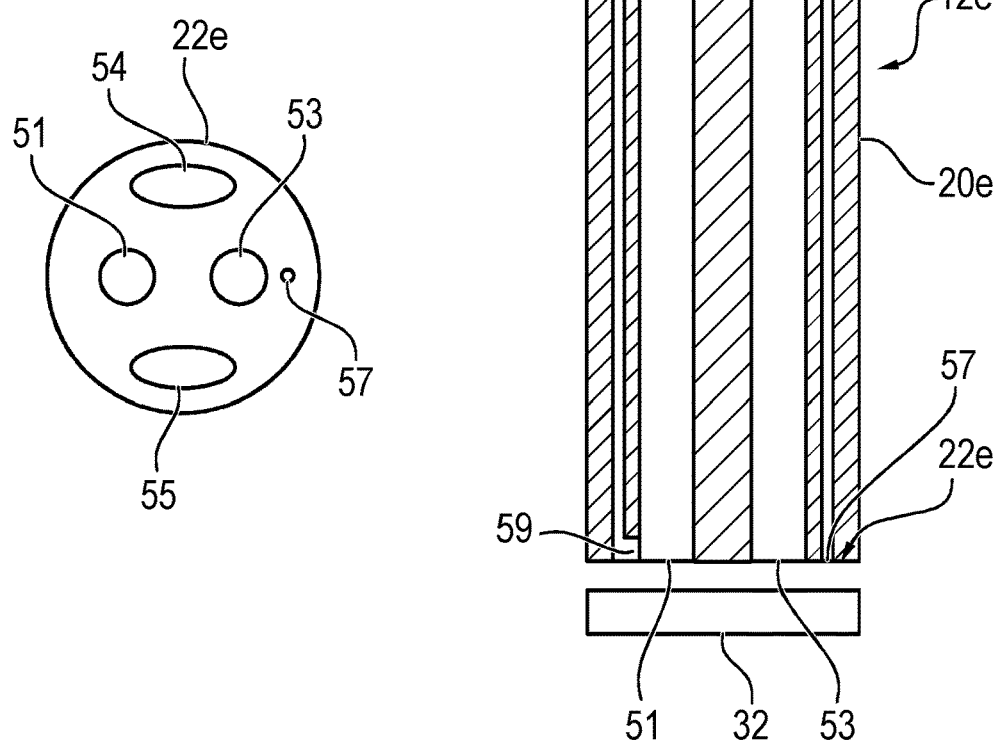
FIG. 6b shows a schematic illustration of the stereoscopic endoscope according to FIG. 6a, as viewed from a distal side.

FIG. 6a shows a schematic sectional view of an arrangement 10e according to a sixth embodiment. The arrangement 10e comprises a stereoscopic endoscope 12e having the first sensor element 40, a second sensor element 42, the first optical fiber 56 and a second optical fiber 58. The arrangement 10e further comprises the endoscope sheath 14 according to FIG. 1, of which in FIG. 6a only the optical element 32 is illustrated, and the output unit 70. The non-sterile endoscope 12e is received in the sterile endoscope sheath 14 and is shielded by it against the environment in a sterile manner. The arrangement 10e according to the sixth embodiment of FIG. 6a differs from the arrangement 10d according to the fourth embodiment of FIG. 4a substantially by providing a second optical fiber 58 and a second sensor element 42.

The endoscope shaft 20e of the endoscope 12e comprises the first observation optical system 50, the second observation optical system 52, the first optical fiber 56 which is optically connected to the first sensor element. The endoscope shaft 20e further comprises the second optical fiber 58 which is optically connected to the second sensor element 42 and which is optically closed at its distal end 59. The endoscope 12e further has an endoscope body 24e arranged at the proximal end of the endoscope shaft 20e, in which body in particular the first sensor element 40, the second sensor element 42, a first image sensor 46e, a second image sensor 47e, the control unit 48, further optical elements such as prisms, lenses or diaphragms assigned to the first observation optical system 50 and generally identified with the reference sign 80 and further optical elements assigned to the second observation optical system 52 and generally provided with the reference sign 82 are arranged.

The electromagnetic radiation in the absorption wavelength range originating from the optical element 32 enters the distal end 57 of the first optical fiber 56 arranged at a distal tip 22e of the endoscope shaft 20e. The first optical fiber 56 guides the electromagnetic radiation in the absorption wavelength range from its distal end 57 to the first sensor element 40 which detects this radiation. From the spectrum of the detected radiation, the control unit 48 determines the temperature of the optical element 32.

Since the second optical fiber 58 is optically closed at its distal end 59, the only radiation guided by the second optical fiber 58 is the heat radiation originating from the closure of the second optical fiber 58 itself. This heat radiation is detected by the second sensor element 42. From the spectrum of the detected radiation, the control unit 48 determines the temperature of the distal end of the endoscope 12e. A heating of the optical element 32 of the endoscope sheath 14 causes, by way of heat conduction, a heating of the distal end of the endoscope 12e. Since the process of the heat conduction requires time, it can be distinguished whether a determined heating of the optical element 32 only takes place for a short period of time, for example by a contact of the optical element 32 with a surgical instrument, such as a laser scalpel, or for a long period of time, for example, by a contamination of the optical element 32 and an absorption of illumination light caused thereby.

The output unit 70 outputs an acoustic and/or optical warning signal when the determined temperature of the optical element 32 of the endoscope sheath 14e and the determined temperature of the optical element of the endoscope 12e each exceed a preset value.

The first observation optical system 50 and the second observation optical system 52 each form an optical channel which guides observation light in the optical wavelength range entering the tip 22e of the endoscope shaft 20e from the distal end of the endoscope shaft 20e to the proximal end of the endoscope shaft 20e, where it enters the further optical elements 80, 82. The observation light guided by the first observation optical system 50 is incident on the first image sensor 46e after passage through the further optical elements 80. The observation light guided by the second observation optical system 52 is incident on the second image sensor 47e after passage through the further optical elements 82. The first and the second image sensor 46e, 47e convert the detected observation light each time into a signal or data. The signals or data are further processed by the control unit 48 for image display. As a result thereof, an observation of an area distal to the tip 22e is possible. Alternatively, the signals or data may also be further processed by a further control unit outside the endoscope 12e for image display. As a result, a stereoscopic observation of an area distal to the tip 22e is possible.

Figure 7A:
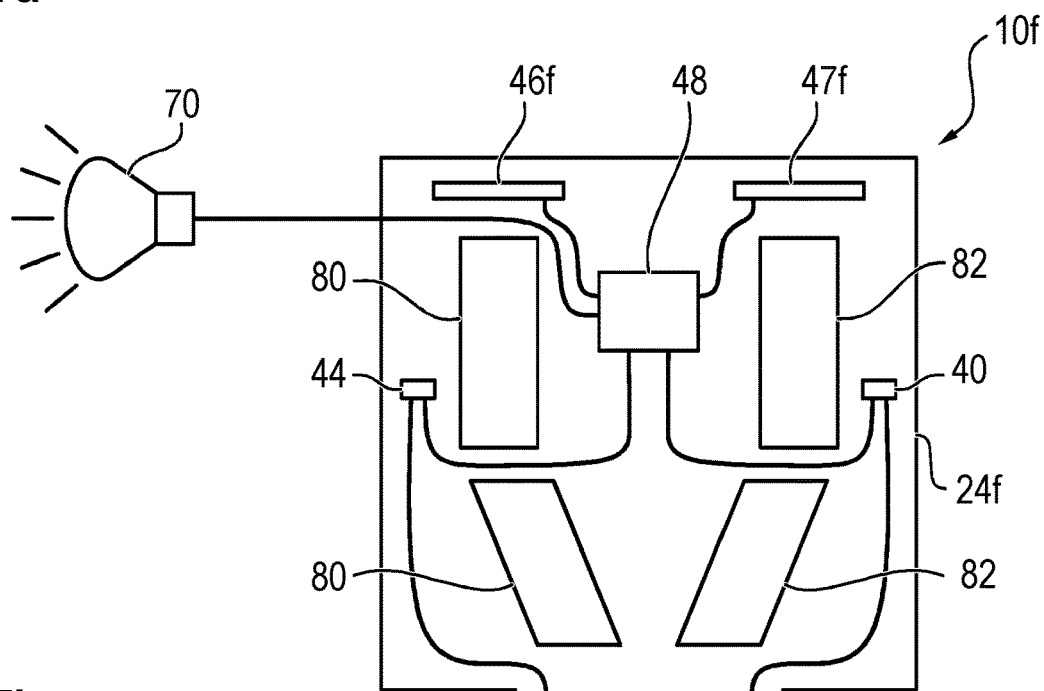
FIG. 7a shows a schematic sectional view of an arrangement with a stereoscopic endoscope according to a seventh embodiment.

FIG. 7a shows a schematic sectional view of an arrangement 10f according to a seventh embodiment. The arrangement 10f comprises a stereoscopic endoscope 12f which has the first sensor element 40, a third sensor element 44, the first optical fiber 56 and a third optical fiber 60. The arrangement 10f further comprises an endoscope sheath, of which in FIG. 7a only one optical element 32 is illustrated, as well as the output unit 70.

From the endoscope sheath, only one optical element 32 is shown in FIG. 7a, which element has an area 74 which is transparent to electromagnetic radiation in the absorption wavelength range. The other structure of the endoscope sheath according to FIG. 7a corresponds to the endoscope sheath 14 according to FIG. 1. The non-sterile endoscope 12f is received in the sterile endoscope sheath and is shielded by it against the environment in a sterile manner.

From the endoscope sheath, only one optical element 32f is shown in FIG. 7a, which element has an area 74 which is transparent to electromagnetic radiation in the absorption wavelength range. The other structure of the endoscope sheath according to FIG. 7a corresponds to the endoscope sheath 14 according to FIG. 1. The non-sterile endoscope 12f is received in the sterile endoscope sheath and is shielded by it against the environment in a sterile manner.

The endoscope shaft 20f of the endoscope 12f comprises the first observation optical system 50, the second observation optical system 52, the first optical fiber 56 which is optically connected to the first sensor element, and the third optical fiber 60 which is optically connected to the third sensor element. The endoscope 12f further has an endoscope body 24f which is arranged at the proximal end of the endoscope shaft 20f and in which in particular the first sensor element 40, the third sensor element 44, a first image sensor 46f, a second image sensor 47f, the control unit 48, the further optical elements 80 that are assigned to the first observation optical system 50 and the further optical elements 82 that are assigned to the second observation optical system 52 are arranged.

The electromagnetic radiation in the absorption wavelength range originating from the optical element 32 enters the distal end 57 of the first optical fiber 56 arranged at a distal tip 22f of the endoscope shaft 20f. The first optical fiber guides the electromagnetic radiation in the absorption wavelength range from its distal end 57 to the first sensor element 40 that detects this radiation. From the spectrum of the detected radiation the control unit 48 determines the temperature of the optical element 32. When the temperature of the optical element 32 determined by the control unit 48 exceeds a preset limit value, the control unit 48 controls the output unit 70 such that it outputs an optical and acoustic warning signal.

A distal end 61 of the third optical fiber 60 is arranged opposite to the area 74 of the optical element 32 that is transparent to electromagnetic radiation in the absorption wavelength range. The third optical fiber 60 guides the radiation entering its distal end 61 to the third sensor element 44. From the spectrum detected by the third sensor element 44, the control unit 48 determines a temperature. The electromagnetic radiation in the absorption wavelength range, which is, for example, emitted by sources in the situs, may freely pass through the optical element 32 in the area 74. Since from the spectrum of this radiation, the temperature of the source in the situs is determined, a temperature measurement in the situs may take place.

The first observation optical system 50 and the second observation optical system 52 each form an optical channel that guides observation light in an optical wavelength range entering the tip 22f of the endoscope shaft 20f from the distal end of the endoscope shaft 20f to the proximal end of the endoscope shaft 20f, where it enters the further optical elements 80, 82. The observation light guided by the first observation optical system 50 is incident on the first image sensor 46f after passing through the further optical elements 80. The observation light guided by the second observation optical system 52 is incident on the second image sensor 47f after passing through the further optical elements 82. The first and the second image sensor 46f, 47f convert the detected observation light each time into a signal. The signals are further processed by the control unit 48 for image display. As a result, an observation of an area distal to the tip 22f is possible. Alternatively, the signals may also be further processed by a further control unit outside the endoscope 12f for image display. As a result thereof, a stereoscopic observation of an area distal to the tip 22f is possible.

Figure 7B:
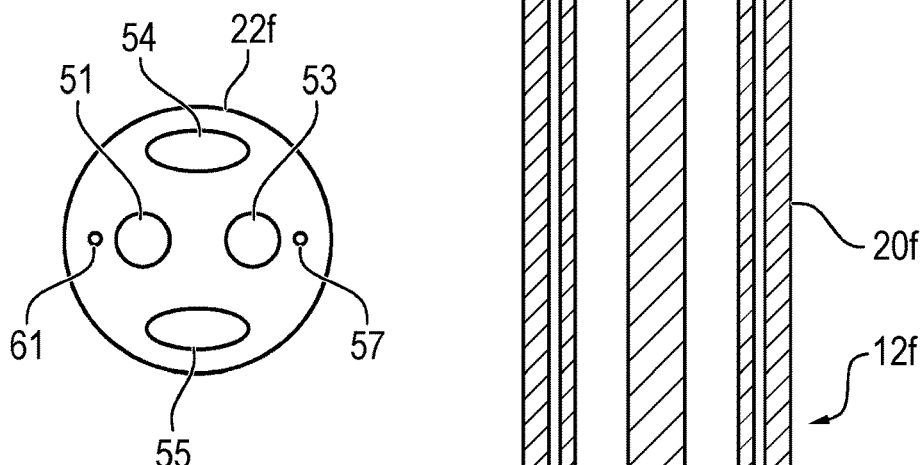
FIG. 7b shows a schematic illustration of the stereoscopic endoscope according to FIG. 7a, as viewed from a distal side in a schematic illustration.

FIG. 7b shows a schematic illustration of the stereoscopic endoscope 12f according to FIG. 7a, as viewed from a distal side. In FIG. 7b, the distal end 51 of the first observation optical system 50 is illustrated to the left of the center of the tip 22f. To the right of the center of the tip 22f, the distal end 53 of the second observation optical system 53 is illustrated. The distal end 57 of the first optical fiber 56 is arranged to the right of the distal end 53 of the second observation optical system 53. The distal end 61 of the third optical fiber 60 is arranged to the left of the distal end 51 of the first observation optical system 50. Above and below the distal end 51 of the first observation optical system 50 and the distal end 53 of the second observation optical system 52, one distal end 54, 55 of an illumination optical system for illuminating the area distal to the tip 22f each is arranged.

Figure 7C:
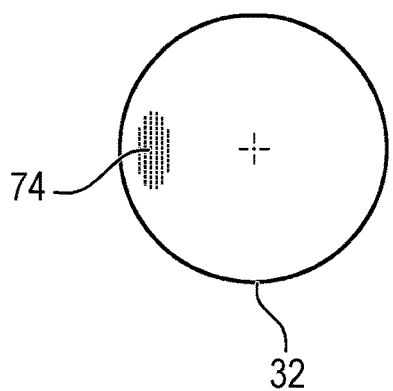
FIG. 7c shows a schematic illustration of an optical element of the endoscope sheath according to FIGS. 7a and 7b, as viewed from a proximal side.

FIG. 7c shows a schematic illustration of the optical element 32 of the endoscope sheath according to FIG. 7a, as viewed from a proximal side. The optical element 32 is transparent to electromagnetic radiation in the absorption wavelength range only in the area 74. The area 74 is arranged on the optical element 32 such that this one is opposite to the distal end 61 of the third optical fiber 60 when the endoscope 12f is received in the endoscope sheath as intended.

The invention claimed is:

1. An arrangement for sterile handling of a non-sterile endoscope in a sterile environment, the arrangement comprising:
   a sterile endoscope sheath having an optical element arranged at a distal end of the sterile endoscope sheath, wherein the optical element absorbs an electromagnetic radiation in an absorption wavelength range lying in a mid-infrared wavelength range, and
   the non-sterile endoscope comprising:
      an endoscope shaft including a first optical fiber having a first distal end and a second optical fiber having a second distal end, the second distal end being optically closed,
      wherein the optical element is optically coupled to the first optical fiber,
      a first electromagnetic radiation sensor element configured to detect the electromagnetic radiation in the absorption wavelength range originating from the optical element, and a second electromagnetic radiation sensor element configured to detect an electromagnetic radiation in the absorption wavelength range originating from the second distal end of the second optical fiber, wherein the second optical fiber is optically connected to the second electromagnetic radiation sensor element and guides the electromagnetic radiation in the absorption wavelength range from the second distal end of the second optical fiber to the second electromagnetic radiation sensor element, wherein the optical element of the non-sterile endoscope is transparent to the electromagnetic radiation in the absorption wavelength range, wherein the non-sterile endoscope is received in the endoscope sheath and is shielded by it against the environment in a sterile manner, and wherein the absorption wavelength range is a wavelength range from 9 μm to 10 μm, from 8 μm to 12 μm or from 8 μm to 14 μm.

2. The arrangement according to claim 1 wherein the optical element is transparent in at least one optical wavelength range outside the absorption wavelength range.

3. The arrangement according to claim 1 further comprising a control unit which determines a temperature of the optical element of the endoscope sheath on the basis of the electromagnetic radiation detected by the first electromagnetic radiation sensor element.

4. The arrangement according to claim 3 further comprising an output unit which outputs an acoustic or optical warning signal when the temperature of the optical element of the endoscope sheath determined with the aid of the control unit reaches and/or exceeds a preset value.

5. The arrangement according to claim 1 wherein the first optical fiber is optically connected to the first electromagnetic radiation sensor element and guides the electromagnetic radiation in the absorption wavelength range entering the distal end of the endoscope shaft to the first electromagnetic radiation sensor element.

6. The arrangement according to claim 1 further comprising a control unit which determines a temperature of the optical element of the endoscope sheath on the basis of the electromagnetic radiation detected by the first electromagnetic radiation sensor element and which determines a temperature of the optical element of the non-sterile endoscope on the basis of the electromagnetic radiation detected by the second electromagnetic radiation sensor element.

7. The arrangement according to claim 6 further comprising an output unit which outputs an acoustic and/or optical warning signal when the determined temperature of the optical element of the endoscope sheath and the determined temperature of the optical element of the non-sterile endoscope each reach and/or exceed a preset value.

8. The arrangement according to claim 1 wherein the optical element of the endoscope sheath has at least one area which is transparent to the electromagnetic radiation in the absorption wavelength range.

9. The arrangement according to claim 8 wherein the non-sterile endoscope has a third electromagnetic radiation sensor element and that the endoscope shaft includes a third optical fiber which is optically connected to the third electromagnetic radiation sensor element, wherein a distal end of the third optical fiber is arranged opposite to the at least one area, and which guides the electromagnetic radiation in the absorption wavelength range entering the distal end of the third optical fiber to the third electromagnetic radiation sensor element.

* * * * *